US011439482B2

(12) United States Patent
Hu et al.

(10) Patent No.: US 11,439,482 B2
(45) Date of Patent: Sep. 13, 2022

(54) INTRAORAL SCANNER

(71) Applicant: QISDA CORPORATION, Taoyuan (TW)

(72) Inventors: Chih-Ming Hu, Taoyuan (TW); Chih-Chieh Tsung, Taoyuan (TW)

(73) Assignee: Qisda Corporation, Taoyuan (TW)

(*) Notice: Subject to any disclaimer, the term of this patent is extended or adjusted under 35 U.S.C. 154(b) by 638 days.

(21) Appl. No.: 16/446,596

(22) Filed: Jun. 19, 2019

(65) Prior Publication Data

US 2019/0388195 A1 Dec. 26, 2019

(30) Foreign Application Priority Data

Jun. 21, 2018 (CN) ............... 201810646232.2

(51) Int. Cl.
| | |
|---|---|
| A61C 9/00 | (2006.01) |
| A61B 1/06 | (2006.01) |
| A61B 1/24 | (2006.01) |
| G02B 27/00 | (2006.01) |

(52) U.S. Cl.
CPC ............ *A61C 9/006* (2013.01); *A61B 1/0623* (2013.01); *A61B 1/0646* (2013.01); *A61B 1/24* (2013.01); *G02B 27/0018* (2013.01)

(58) Field of Classification Search
None
See application file for complete search history.

(56) References Cited

U.S. PATENT DOCUMENTS

| | | | | |
|---|---|---|---|---|
| 2008/0063998 | A1* | 3/2008 | Liang ............... | G01N 21/6456 433/29 |
| 2010/0268033 | A1* | 10/2010 | Yamamoto ......... | A61B 1/00177 600/178 |
| 2011/0221879 | A1* | 9/2011 | Schmidt ............ | A61B 1/0669 348/E7.085 |
| 2018/0081163 | A1* | 3/2018 | Lin ..................... | A61B 1/051 |
| 2021/0068633 | A1* | 3/2021 | Morita ............... | A61B 1/00179 |

* cited by examiner

*Primary Examiner* — Rebecca A Volentine

(57) ABSTRACT

An intraoral scanner includes a casing, a light source disposed in the casing, a reflection plate obliquely disposed in the casing for reflecting light of the light source to an object to be scanned through an opening of the casing, a transparent plate, and a receiver adjacent to the light source. A projection optical axis of the light source forms a first oblique angle with a receiving optical axis of the receiver. The receiver receives light after being incident to the object to be scanned and then reflected to the receiver by the reflection plate. The transparent plate is disposed between the light source and the reflection plate or covers the opening. The projection optical axis forms a second oblique angle with a norm of the transparent plate to make a reflection angle range of light reflected by the transparent plate fall outside a receiving angel range of the receiver.

6 Claims, 4 Drawing Sheets

INTRAORAL SCANNER

BACKGROUND OF THE INVENTION

1. Field of the Invention

The present invention relates to an intraoral scanner, and more specifically, to an intraoral scanner having a light source forming an oblique angle with a transparent plate.

2. Description of the Prior Art

In general, during the 3D tooth model forming process, a user (e.g. a medical personnel) usually holds an IOS (Intraoral Scanner) by his hand to perform optical scanning on upper and lower jaw regions in an oral cavity of a patient. The optical scanning method involves utilizing a light source in the intraoral scanner to project a scanning light (e.g. projecting a structured light with a specific pattern by the DLP (Digital Light Processing) technique or projecting a linear laser beam by a laser light source), utilizing a reflection plate to reflect the scanning light to pass through a light exit opening of the intraoral scanner and then be incident to teeth of the patient, and utilizing a receiver in the intraoral scanner to receive the scanning light after being incident to the teeth and then reflected to the receiver by the reflection plate. In such a manner, a 3D tooth model could be displayed on a monitor for the subsequent tooth implanting or dental prosthesis manufacturing process after the related image identification and combination processes are completed by a terminal host.

However, during the aforesaid projection process, reflection of the scanning light usually occurs when the scanning light passes through a polarizer disposed between the light source and the reflection plate or a transparent protection sheet covering the light exit opening, so as to make partial scanning light incident back to the receiver to generate light-receiving noise or serious ghost images. As such, the prior art causes distortion or even failure of image identification and combination for the 3D tooth model.

SUMMARY OF THE INVENTION

The present invention provides an intraoral scanner. The intraoral scanner includes a casing, a light source, a reflection plate, a receiver, and a transparent plate. The casing has an opening. The light source is disposed in the casing. The reflection plate is obliquely disposed in the casing corresponding to the opening for reflecting light of the light source to an object to be scanned through the opening. The receiver is disposed in the casing and located at a side of the light source. A projection optical axis of the light source forms a first oblique angle with a receiving optical axis of the receiver. The receiver has a receiving angle range for receiving light after being incident to the object to be scanned and then reflected to the receiver by the reflection plate. The transparent plate is disposed between the light source and the reflection plate or covers the opening. The projection optical axis forms a second oblique angle with a norm of the transparent plate to make a reflection angle range of light reflected by the transparent plate fall outside the receiving angle range.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
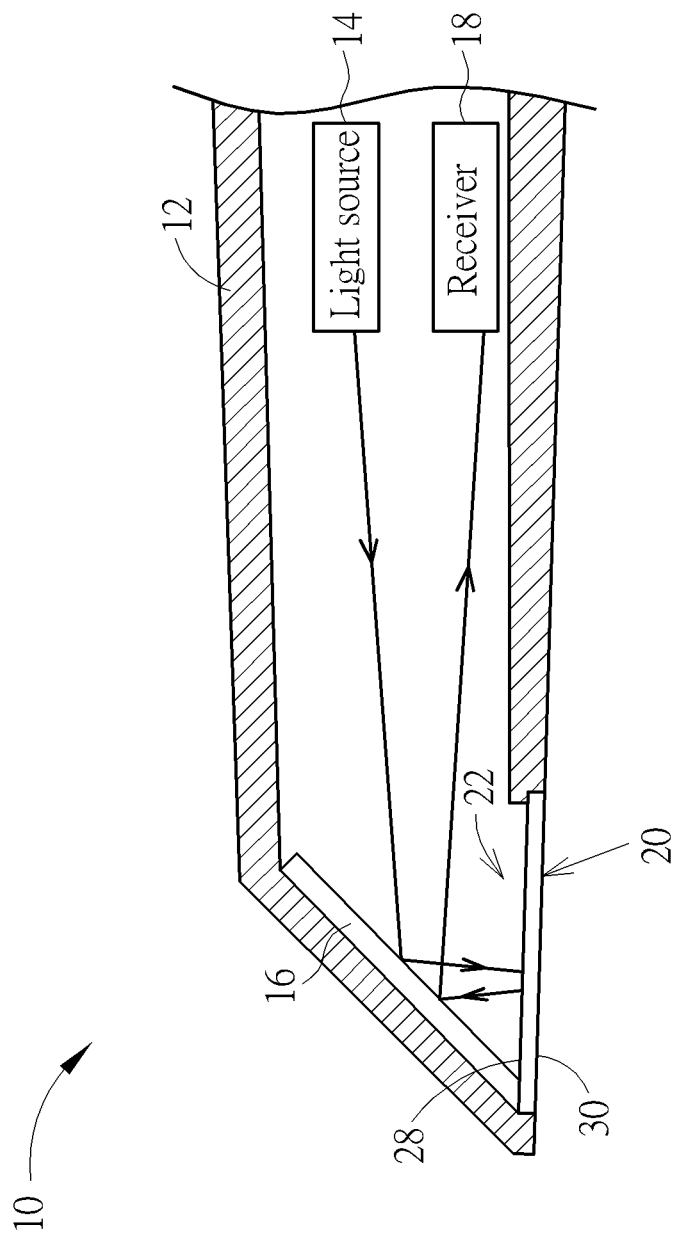
FIG. 1 is a partial internal diagram of an intraoral scanner according to an embodiment of the present invention.
Figure 2:
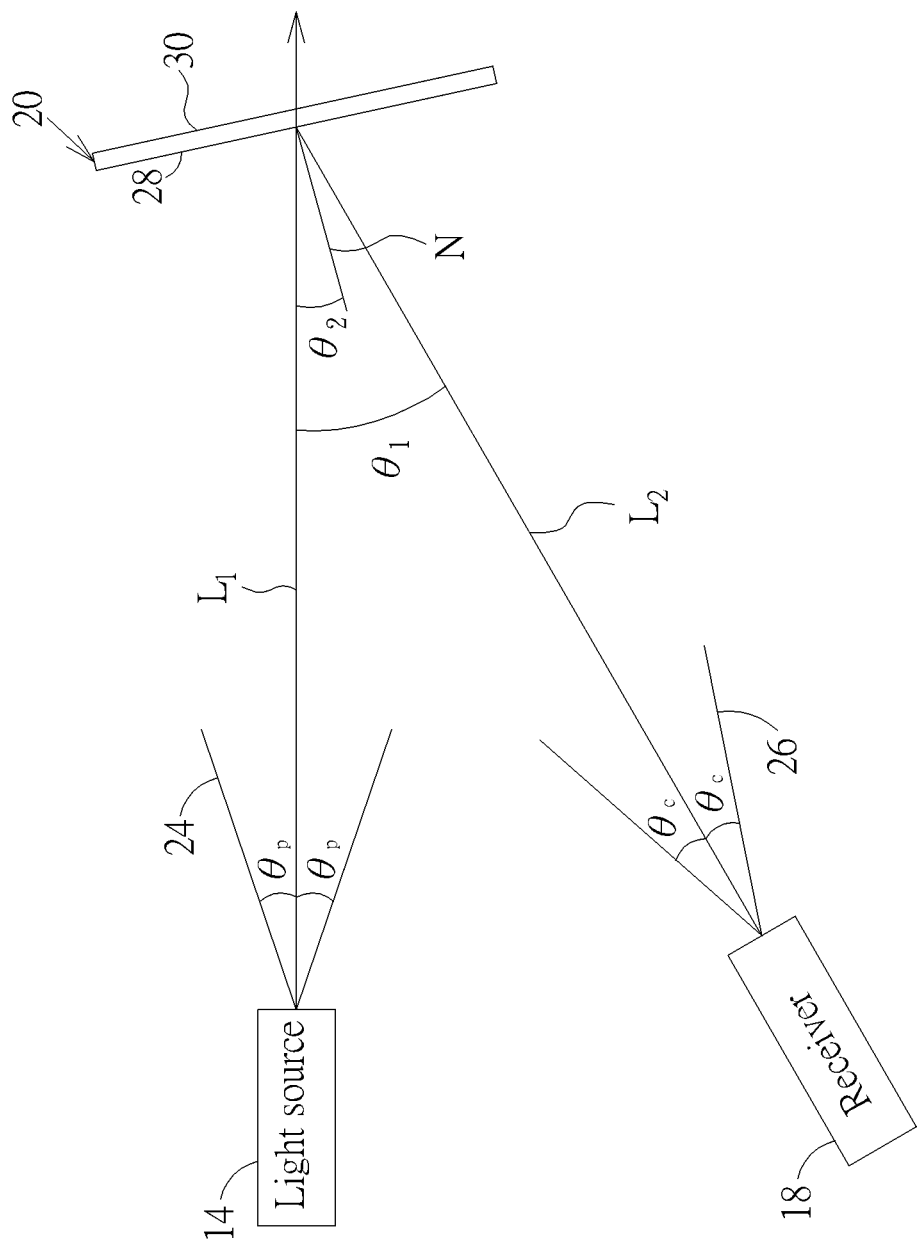
FIG. 2 is a light path diagram of a light source, a receiver, and a transparent plate in FIG. 1.

Please refer to FIG. 1 and FIG. 2. FIG. 1 is a partial internal diagram of an intraoral scanner 10 according to an embodiment of the present invention. FIG. 2 is a light path diagram of a light source 14, a receiver 18, and a transparent plate 20 in FIG. 1. The intraoral scanner 10 adopts a conventional tooth model scanning technique (e.g. projecting a structured light with a specific pattern by the DLP technique or projecting a linear laser beam by a laser light source) to perform optical scanning on an object to be scanned (e.g. teeth of a patient). As for the related description for the optical scanning principle, it is commonly seen in the prior art and omitted herein. As shown in FIG. 1 and FIG. 2, the intraoral scanner 10 includes a casing 12, the light source 14, a reflection plate 16, the receiver 18, and the transparent plate 20. The casing 12 has an opening 22 such that light of the light source 14 can pass through the opening 22 to be incident to the object to be scanned. The light source 14 (e.g. an LED (Light Emitting Diode) light source or a laser light source) is disposed in the casing 12 and has a light-emitting angle range 24 for emitting light along a projection optical axis $L_1$. The reflection plate 16 is obliquely disposed in the casing 12 corresponding to the opening 22 for reflecting the light of the light source 14 to the object to be scanned through the opening 22. The receiver 18 is disposed in the casing 12 and located at a side of the light source 14. The projection optical axis $L_1$ of the light source 14 forms a first oblique angle $\theta_1$ with a receiving optical axis $L_2$ of the receiver 18. The receiver 18 has a receiving angle range 26 for receiving light after being incident to the object to be scanned and then reflected to the receiver 18 by the reflection plate 16. In such a manner, a corresponding 3D tooth model can be displayed on a monitor for the subsequent tooth implanting or dental prosthesis manufacturing process after the related image identification and combination processes are completed by a terminal host.

Figure 3:
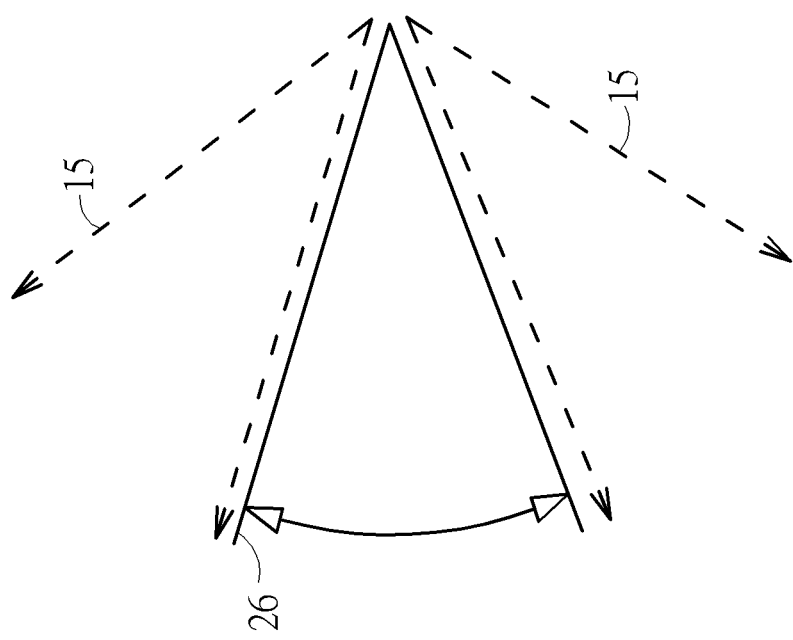
FIG. 3 is a diagram of a reflection angle range of light in FIG. 2 falling outside a receiving angle range of the receiver.

As shown in FIG. 1, the transparent plate 20 could preferably be a transparent protection sheet to cover the opening 22 for generating the dustproof effect, and the projection optical axis $L_1$ of the light source 14 forms a second oblique angle $\theta_2$ with a norm N of the transparent plate 20 to make light reflected by the transparent plate 20 fall outside the receiving angle range 26. To be more specific, please refer to FIG. 2 and FIG. 3. FIG. 3 is a diagram of a reflection angle range 15 of light in FIG. 2 falling outside the receiving angle range 26. As shown in FIG. 2 and FIG. 3, the transparent plate 20 has a light entrance surface 28 and a light exit surface 30. The light entrance surface 28 is parallel to the light exit surface 30 and has the norm N to form the second oblique angle $\theta_2$ with the projection optical axis $L_1$. In this embodiment, the intraoral scanner 10 could preferably adopt the design that a light receiving/emitting range is defined by a light-emitting half angle. That is, a light-emitting half angle of the light source 14 could be set as $\theta_p$ to define a light-emitting angle range 24 of the light source 14 relative to the projection optical axis $L_1$ as $(-\theta_p \sim \theta_p)$, a light-receiving half angle of the receiver 18 is set as $\theta_c$ to define the receiving angle range 26 relative to the receiving optical axis $L_2$ as $(-\theta_c-\theta_1 \sim -\theta_c-\theta_1)$, and the reflection angle range 15 relative to the norm N is defined as $(-\theta_p-2\theta_2 \sim -\theta_p-2\theta_2)$ by the second oblique angle $\theta_2$ according to the law of reflection. According to the aforesaid setting of the reflection angle range 15 falling outside the receiving angle range 26 (i.e. as shown in FIG. 3, the minimum reflection angle of the reflection angle range 15 is larger than or equal to the maximum receiving angle of the receiving angle range 26, or the maximum reflection angle of the reflection angle range 15 is less than or equal to the minimum receiving angle of the receiving angle range 26), the present invention could derive the following equations:

$$(-\theta_p-2\theta_2) \geq (+\theta_c-\theta_1); \text{ or}$$

$$(+\theta_p-2\theta_2) \leq (-\theta_c-\theta_1).$$

In such a manner, the intraoral scanner 10 can calculate an inclination adjustment range (as shown below) of the second oblique angle $\theta_2$ formed by the norm N of the transparent plate 20 and the projection optical axis $L_1$ according to the aforesaid equations, so as to ensure that the reflection angle range 15 of the light reflected by the transparent plate 20 can fall outside the receiving angle range 26 of the receiver 18 by appropriately adjusting the second oblique angle $\theta_2$. The inclination adjustment range of the second oblique angle $\theta_2$ is provided as follows:

$$\theta_2 \leq (-\theta_p-\theta_c+\theta_1)/2; \text{ or}$$

$$\theta_2 \geq (\theta_p+\theta_c+\theta_1)/2.$$

For example, it is assumed that the light-emitting half angle $\theta_p$ of the light source 14 is equal to 3.47° to define the light emitting range 24 relative to the projection optical axis $L_1$ as $(-3.47° \sim 3.47°)$, the first oblique angle $\theta_1$ is equal to 8.3°, the light-receiving half angle $\theta_c$ of the receiver 18 is equal to 3.56° to define the light receiving angle range 26 relative to the receiving optical axis $L_2$ as $(-3.56°-8.3° \sim 3.56°-8.3°)$, and the reflection angle range 15 relative to the norm N is defined as $(-3.47°-2\theta_2 \sim 3.47°-2\theta_2)$ by the second oblique angle $\theta_2$. Accordingly, the intraoral scanner 10 can calculate the inclination adjustment range of the second oblique angle $\theta_2$ as $(\theta_2 \leq 0.635°$ or $\theta_2 \geq 7.665°)$ to help a user appropriately adjust inclination of the transparent plate 20. As such, after the second oblique angle $\theta_2$ is adjusted to conform to the aforesaid inclination adjustment range, the light-receiving noise or ghost image problem can be efficiently solved.

In practical application, if the second oblique angle $\theta_2$ is equal to 4.15° according to an actual measurement result, the light-receiving noise or ghost image problem still occurs in an image received by the receiver 18 since the second oblique angle $\theta_2$ does not fall within the aforesaid inclination adjustment range (i.e. $\theta_2 \leq 0.635°$ or $\theta_2 \geq 7.665°$). In this condition, the user can tilt the transparent plate 20 as shown in FIG. 1 upward by 5° (but not limited thereto, meaning that the tilted angle can be increased or decreased according to the practical application of the intraoral scanner 10) according to the aforesaid inclination adjustment range, so that the second oblique angle $\theta_2$ can be adjusted to −0.85° to conform to the aforesaid inclination adjustment range (i.e. $\theta_2 \leq 0.635°$ or $\theta_2 \geq 7.665°$).

In such a manner, the present invention can surely prevent light reflected by the transparent plate 20 in the intraoral scanner 10 from falling within the receiving angle range 26 of the receiver 18, so as to efficiently solve the prior art problem that distortion or even failure of image identification and combination for the 3D tooth model occurs due to light-receiving noise or serious ghost images. Accordingly, the present invention can greatly improve the image identification and tooth-model manufacturing quality of the intraoral scanner 10.

The present invention can also be applied to other optical reflective member disposed in the intraoral scanner. For example, in another embodiment, the transparent plate could include a polarizer for changing polarity of light projected by the light source of the intraoral scanner. The polarizer is disposed between the light source and the reflection plate. In this embodiment, the present invention can calculate the inclination adjustment range of the oblique angle formed by the norm of the polarizer and the projection optical axis of the light source, so as to help the user appropriately adjust inclination of the polarizer according to the inclination adjustment range of the oblique angle for efficiently preventing the light-receiving noise or ghost image problem. As for other related description for this embodiment, it could be reasoned by analogy according to the aforesaid embodiment and omitted herein.

Figure 4:
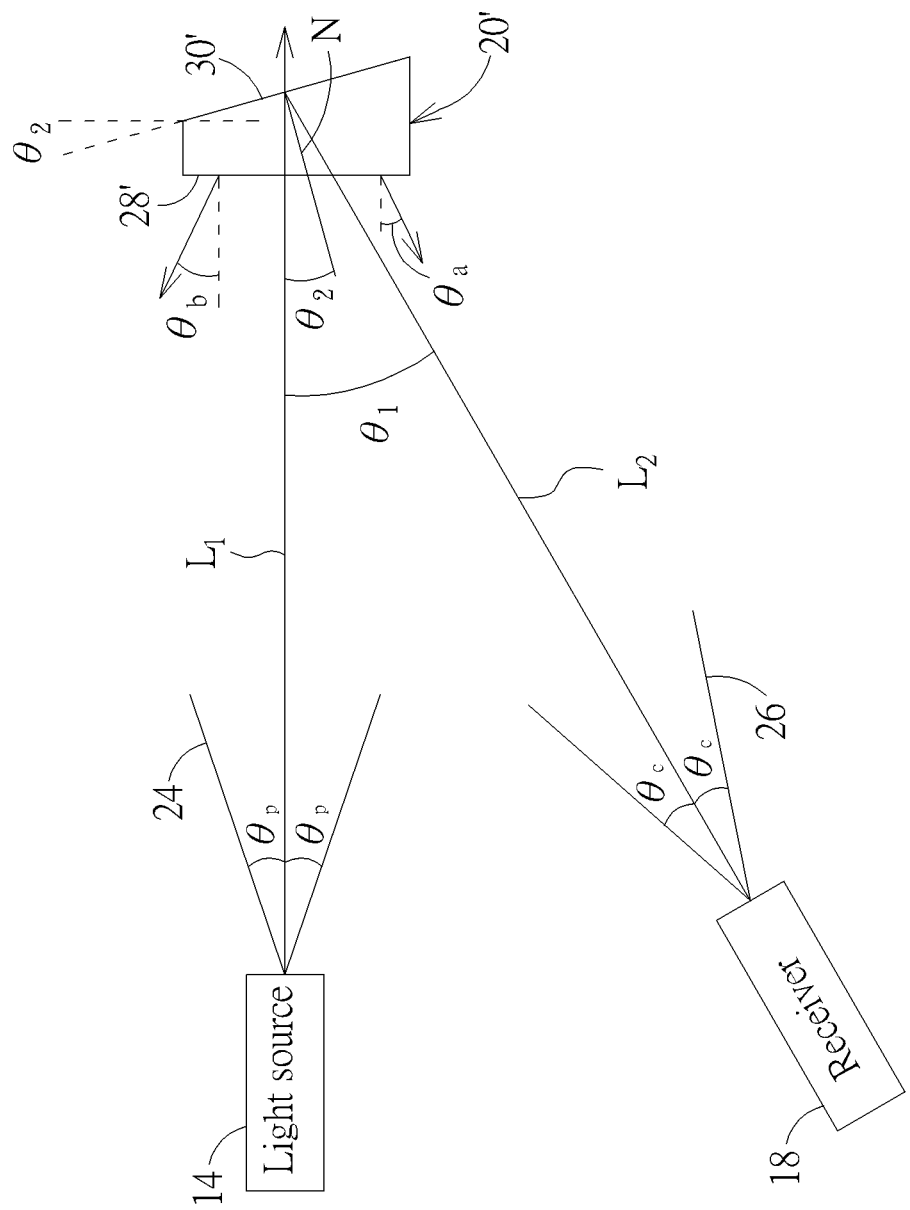
FIG. 4 is a light path diagram of a transparent plate, the light source, and the receiver according to another embodiment of the present invention.

It should be mentioned that the structural design of the transparent plate is not limited to the aforesaid embodiment. For example, please refer to FIG. 4, which is a light path diagram of a transparent plate 20', the light source 14, and the receiver 18 according to another embodiment of the present invention. Components both mentioned in this embodiment and the aforesaid embodiments represent components with similar functions or structures, and the related description is omitted herein. As shown in FIG. 4, the transparent plate 20' could have a light entrance surface 28' and a light exit surface 30'. The light entrance surface 28' is perpendicular to the projection optical axis $L_1$. The light exit surface 30' is tilted outwardly relative to the light entrance surface 28' by the second oblique angle $\theta_2$. The light exit surface 30' has the norm N to form the second oblique angle $\theta_2$ with the projection optical axis $L_1$. The projection optical axis $L_1$ of the light source 14 forms the first oblique angle $\theta_1$ with the receiving optical axis $L_2$ of the receiver 18. In practical application, it is assumed that a refractive index of the transparent plate 20' is set as n (the refractive index of air outside the transparent plate 20' is 1), the light-emitting half angle of the light source 14 is set as $\theta_p$ to define the light-emitting angle range 24 relative to the projection optical axis $L_1$ as $(-\theta_p \sim \theta_p)$, the light-receiving half angle of the receiver 18 is set as $\theta_c$ to define the receiving angle range 26 relative to the receiving optical axis $L_2$ as $(-\theta_c-\theta_1 \sim -\theta_c-\theta_1)$, and an upper reflection angle and a lower reflection angle of a reflection angle range of light reflected by the transparent plate 20' relative to the projection optical axis $L_1$ are set as $\theta_b$ and $\theta_a$ respectively. According to the laws of refraction and reflection and the setting of the reflection angle range falling outside the receiving angle range 26 (i.e. the minimum reflection angle of the reflection angle range is larger than or equal to the maximum receiving angle of the receiving angle range 26, or the maximum reflection angle of the reflection angle range is less than or equal to the minimum receiving angle of the receiving angle range 26), the present invention could derive the following equations:

$$\theta_a = \sin^{-1}[\sin \theta_p * \cos(2\theta_2) + (\sqrt{n^2 - \sin^2 \theta_p}) * \sin(2\theta_2)];$$

$$\theta_b = \sin^{-1}[\sin \theta_p * \cos(2\theta_2) - (\sqrt{n^2 - \sin^2 \theta_p}) * \sin(2\theta_2)];$$
and $$\theta_b \geq (\theta_c - \theta_1) \text{ or } \theta_a \leq (-\theta_c - \theta_1).$$

In such a manner, the present invention can utilize a computer to calculate the inclination adjustment range of the second oblique angle $\theta_2$ formed by the norm N of the transparent plate 20' and the projection optical axis $L_1$, so as to help the user appropriately adjust inclination of the transparent plate 20'. As such, after the second oblique angle $\theta_2$ is adjusted to conform to the aforesaid inclination adjustment range for ensuring that the reflection angle range of light reflected by the transparent plate 20' can fall outside the receiving angle range 26 of the receiver 18, the present invention can efficiently solve the prior art problem that distortion or even failure of image identification and combination for the 3D tooth model occurs due to light-receiving noise or serious ghost images.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An intraoral scanner comprising:
   a casing having an opening;
   a light source disposed in the casing;
   a reflection plate obliquely disposed in the casing corresponding to the opening for reflecting light of the light source to an object to be scanned through the opening;
   a receiver disposed in the casing and located at a side of the light source, a projection optical axis of the light source forming a first oblique angle with a receiving optical axis of the receiver, the receiver having a receiving angle range for receiving light after being incident to the object to be scanned and then reflected to the receiver by the reflection plate; and
   a transparent plate disposed between the light source and the reflection plate or covering the opening, the transparent plate having a light entrance surface and a light exit surface, the light entrance surface being parallel to the light exit surface, the projection optical axis forming a second oblique angle with a norm of the light entrance surface to make a reflection angle range of light reflected by the transparent plate fall outside the receiving angle range;
   wherein a light-emitting half angle of the light source is set as $\theta_P$ to define a light-emitting angle range of the light source relative to the projection optical axis as $(-\theta_P \sim \theta_P)$, the first oblique angle is set as $\theta_1$ and a light-receiving half angle of the receiver is set as $\theta_c$ to define the receiving angle range relative to the receiving optical axis as $(-\theta_c-\theta_1 \sim \theta_c-\theta_1)$, the second oblique angle is set as $\theta_2$ to define the reflection angle range as $(-\theta_p-2\theta_2 \sim \theta_p-2\theta_2)$ relative to the norm, and the second oblique angle conforms to the following equations:

$(-\theta_p-2\theta_2) \geq (+\theta_c-\theta_1)$; or $(+\theta_p-2\theta_2) \leq (-\theta_c-\theta_1)$.

2. The intraoral scanner of claim 1, wherein the transparent plate comprises a polarizer and is disposed between the light source and the reflection plate.

3. The intraoral scanner of claim 1, wherein the transparent plate is a transparent protection sheet covering the opening.

4. An intraoral scanner comprising:
   a casing having an opening;
   a light source disposed in the casing;
   a reflection plate obliquely disposed in the casing corresponding to the opening for reflecting light of the light source to an object to be scanned through the opening;
   a receiver disposed in the casing and located at a side of the light source, a projection optical axis of the light source forming a first oblique angle with a receiving optical axis of the receiver, the receiver having a receiving angle range for receiving light after being incident to the object to be scanned and then reflected to the receiver by the reflection plate; and
   a transparent plate disposed between the light source and the reflection plate or covering the opening, the transparent plate having a light entrance surface and a light exit surface, the light entrance surface being perpendicular to the projection optical axis, the projection optical axis forming a second oblique angle with a norm of the light entrance surface to make a reflection angle range of light reflected by the transparent plate fall outside the receiving angle range, and the light exit surface being tilted outwardly relative to the light entrance surface by the second oblique angle;
   wherein a refractive index of the transparent plate is set as n, a light-emitting half angle of the light source is set as $\theta_P$ to define a light-emitting angle range of the light source relative to the projection optical axis as $(-\theta_P \sim \theta_P)$, the first oblique angle is set as $\theta_1$ and a light-receiving half angle of the receiver is set as $\theta_c$ to define the receiving angle range relative to the receiving optical axis as $(-\theta_c-\theta_1 \sim \theta_c-\theta_1)$, the second oblique angle is set as $\theta_2$, and an upper reflection angle and a lower reflection angle of the reflection angle range relative to the projection optical axis are set as $\theta_b$ and $\theta_a$ respectively and conform the following equations:

$\theta_a = \sin^{-1}[\sin\theta_p * \cos(2\theta_2) + (\sqrt{(n^2-\sin^2\theta_p)}) * \sin(2\theta_2)]$;

$\theta_b = \sin^{-1}[\sin\theta_p * \cos(2\theta_2) - (\sqrt{(n^2-\sin^2\theta_p)}) * \sin(2\theta_2)]$; and $\theta_b \geq (\theta_c-\theta_1)$ or $\theta_a \leq (-\theta_c-\theta_1)$.

5. The intraoral scanner of claim 4, wherein the transparent plate comprises a polarizer and is disposed between the light source and the reflection plate.

6. The intraoral scanner of claim 4, wherein the transparent plate is a transparent protection sheet covering the opening.

* * * * *